(12) United States Patent
Galloway et al.

(10) Patent No.: US 9,061,121 B2
(45) Date of Patent: Jun. 23, 2015

(54) TARGETING THERAPEUTIC AGENTS

(75) Inventors: Niall Galloway, Atlanta, GA (US);
James Galloway, Atlanta, GA (US);
Patrick McHugh, Sugar Hill, GA (US);
Brian Collins, Centennial, CO (US)

(73) Assignee: Emory University, Atlanta, GA (US)

( * ) Notice: Subject to any disclaimer, the term of this patent is extended or adjusted under 35 U.S.C. 154(b) by 393 days.

(21) Appl. No.: 13/388,695

(22) PCT Filed: Aug. 3, 2010

(86) PCT No.: PCT/US2010/044224
§ 371 (c)(1),
(2), (4) Date: Feb. 3, 2012

(87) PCT Pub. No.: WO2011/017306
PCT Pub. Date: Feb. 10, 2011

(65) Prior Publication Data
US 2012/0130282 A1    May 24, 2012

Related U.S. Application Data

(60) Provisional application No. 61/230,905, filed on Aug. 3, 2009.

(51) Int. Cl.
*A61M 5/00* (2006.01)
*A61M 31/00* (2006.01)
(Continued)

(52) U.S. Cl.
CPC ............... *A61M 29/02* (2013.01); *A61B 17/42* (2013.01); *A61F 2250/0067* (2013.01); *A61B 2018/00523* (2013.01); *A61B 2018/00517* (2013.01); *A61B 17/4241* (2013.01); *A61B 1/307* (2013.01); *A61B 17/3403* (2013.01); *A61B 2017/00805* (2013.01); *A61B 2017/3407* (2013.01); *A61M 25/0084* (2013.01); *A61M 25/01* (2013.01)

(58) Field of Classification Search
CPC ............... A61B 17/42; A61B 17/4241; A61B 17/3403; A61B 17/3405; A61B 2017/00805; A61B 2018/00523; A61B 2018/00517; A61F 2250/0067; A61M 29/00
USPC ............ 600/29, 104, 135, 587; 604/116, 500, 604/515, 517
See application file for complete search history.

(56) References Cited

U.S. PATENT DOCUMENTS

| 5,454,365 A | 10/1995 | Bonutti |
|---|---|---|
| 5,887,593 A | 3/1999 | Levius |

(Continued)

FOREIGN PATENT DOCUMENTS

| WO | 9947069 A1 | 9/1999 |
|---|---|---|
| WO | 0122897 A1 | 4/2001 |

(Continued)

OTHER PUBLICATIONS

Supplementary European Search Report for EP Serial No. 10807014.5; Jan. 2, 2013; 11 pgs.

(Continued)

*Primary Examiner* — Devin Henson
(74) *Attorney, Agent, or Firm* — Emory Patent Group

(57) ABSTRACT

Provided are devices, systems, and methods for targeted administration of therapeutic agents to a subject. For example, provided are devices, systems, and methods for targeting the administration of peri-urethral bulking agents.

58 Claims, 8 Drawing Sheets

(51) Int. Cl.
*A61F 2/00* (2006.01)
*A61B 5/103* (2006.01)
*A61B 5/117* (2006.01)
*A61M 29/02* (2006.01)
*A61B 17/34* (2006.01)
*A61M 25/00* (2006.01)
*A61M 25/01* (2006.01)
*A61B 17/42* (2006.01)
*A61B 18/00* (2006.01)
*A61B 1/307* (2006.01)
*A61B 17/00* (2006.01)

(56) References Cited

U.S. PATENT DOCUMENTS

| | | |
|---|---|---|
| 5,957,920 A | 9/1999 | Baker |
| 6,053,899 A | 4/2000 | Slanda et al. |
| 6,071,230 A * | 6/2000 | Henalla ............ 600/29 |
| 6,398,758 B1 | 6/2002 | Jacobsen et al. |
| 6,432,045 B2 * | 8/2002 | Lemperle et al. ............ 600/135 |
| 6,517,534 B1 | 2/2003 | McGovern et al. |
| 6,517,566 B1 | 2/2003 | Hovland et al. |
| 6,726,699 B1 | 4/2004 | Wright et al. |
| 6,855,160 B1 | 2/2005 | Gambale et al. |
| 7,278,985 B2 | 10/2007 | Agerup |
| 7,291,129 B2 * | 11/2007 | Li et al. ............ 604/164.01 |
| 7,292,885 B2 | 11/2007 | Scott et al. |
| 7,341,576 B2 | 3/2008 | Erickson et al. |
| 7,488,313 B2 | 2/2009 | Segal et al. |
| 7,517,342 B2 | 4/2009 | Scott et al. |
| 7,527,610 B2 | 5/2009 | Erickson |
| 7,753,876 B2 | 7/2010 | Cervantes et al. |
| 7,892,205 B2 | 2/2011 | Palasis et al. |
| 8,002,735 B2 | 8/2011 | Del Vecchio |
| 8,052,669 B2 | 11/2011 | Lee-Sepsick et al. |
| 2005/0043680 A1 | 2/2005 | Segal et al. |
| 2005/0124852 A1 | 6/2005 | Bolmsjo et al. |
| 2008/0058590 A1 | 3/2008 | Saadat et al. |
| 2008/0171905 A1 * | 7/2008 | Anderson ............ 600/29 |
| 2009/0112184 A1 | 4/2009 | Fierens et al. |
| 2009/0281486 A1 | 11/2009 | Ducharme |
| 2009/0312696 A1 | 12/2009 | Copa et al. |
| 2010/0168714 A1 | 7/2010 | Burke et al. |
| 2010/0312171 A1 | 12/2010 | Joshi et al. |
| 2011/0071468 A1 | 3/2011 | Utley et al. |
| 2011/0184338 A1 | 7/2011 | McKay |

FOREIGN PATENT DOCUMENTS

| | | |
|---|---|---|
| WO | 0174418 A2 | 10/2001 |
| WO | 2004037313 A2 | 5/2004 |
| WO | 2006133193 A1 | 12/2006 |
| WO | 2007137148 A2 | 11/2007 |

OTHER PUBLICATIONS

International Search Report of PCT/US2010/044224; Apr. 27, 2011; 7 pgs.
Written Opinion of PCT/US2010/044224; Apr. 27, 2011; 4 pgs.
International Preliminary Report on Patentability of PCT/US2010/044224; Feb. 7, 2012; 5 pgs.

* cited by examiner

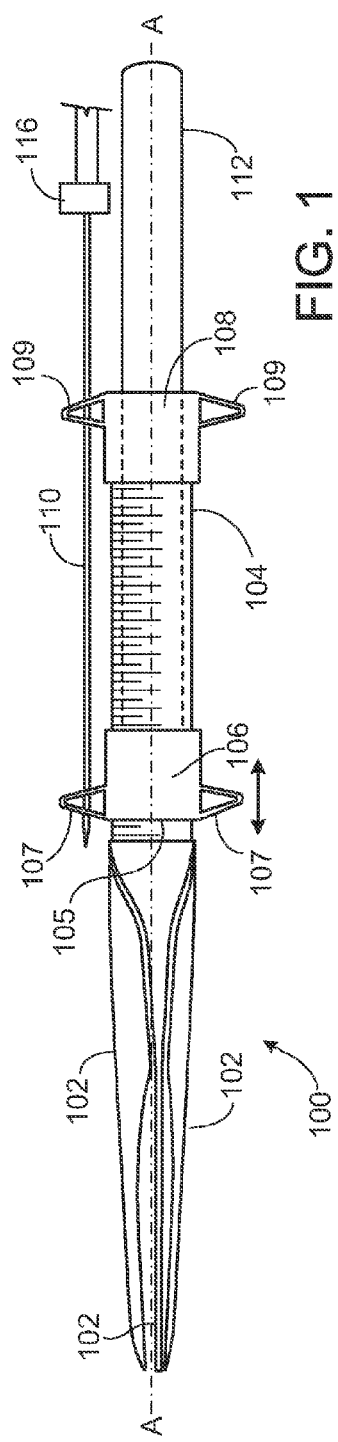
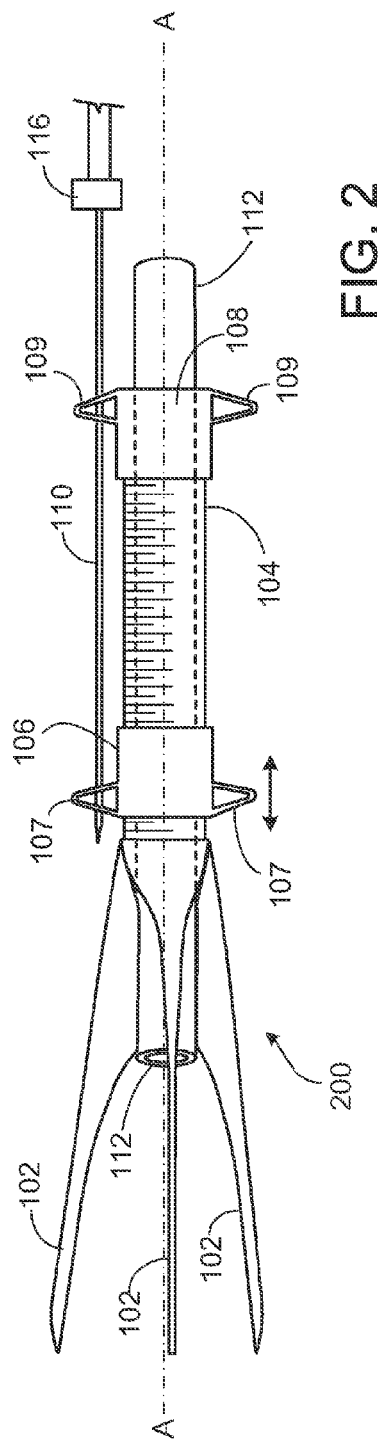

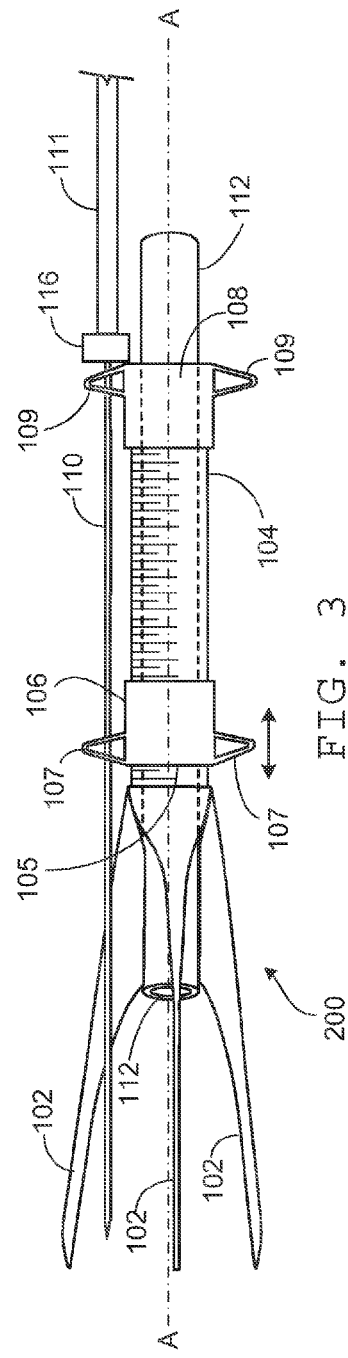
FIG. 3
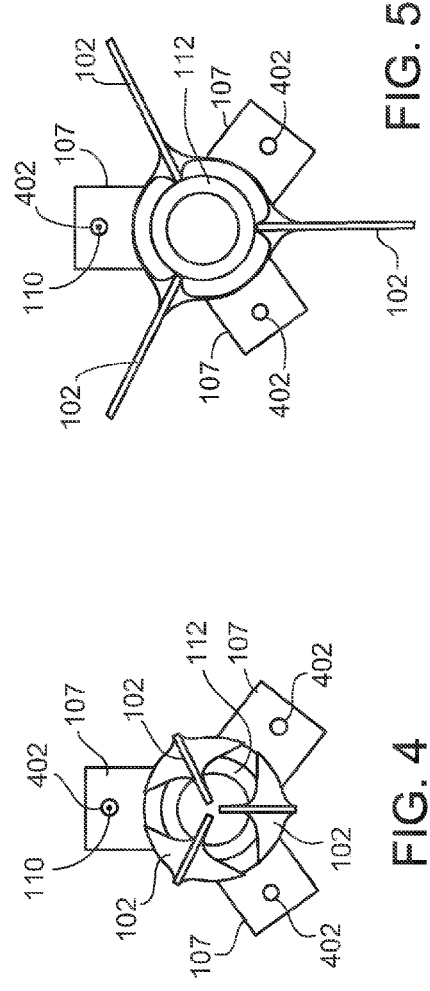
FIG. 4
FIG. 5

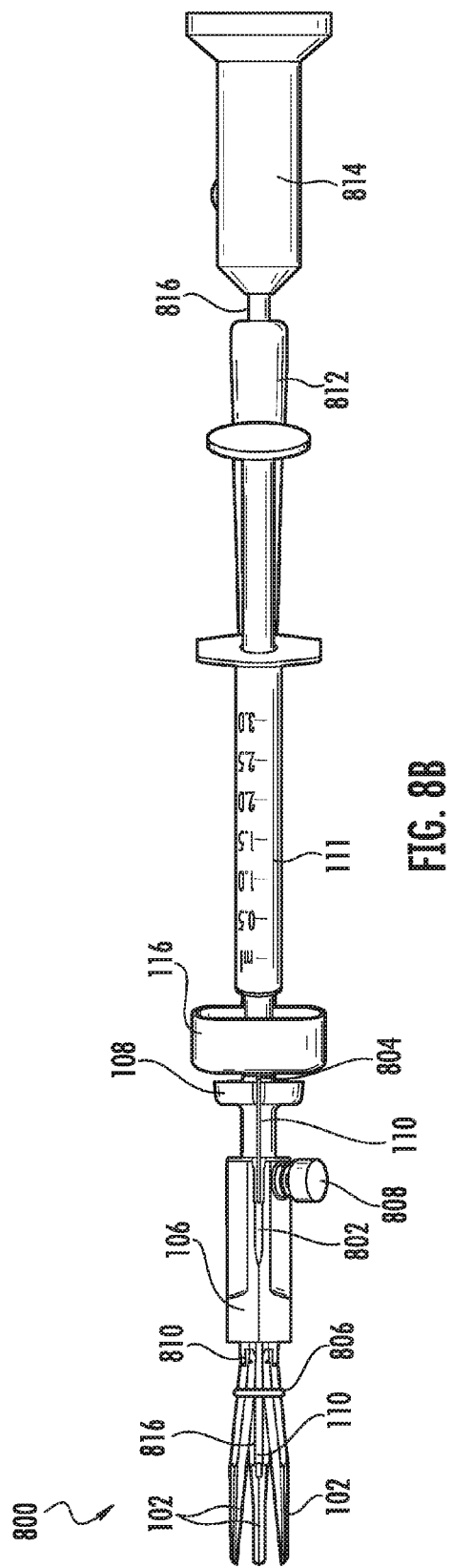

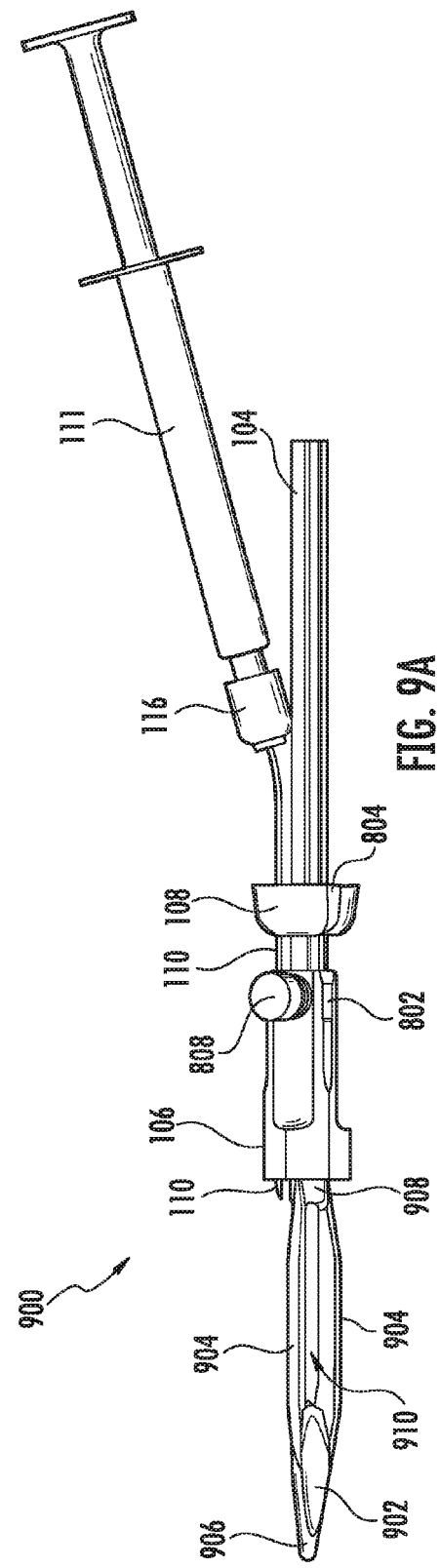

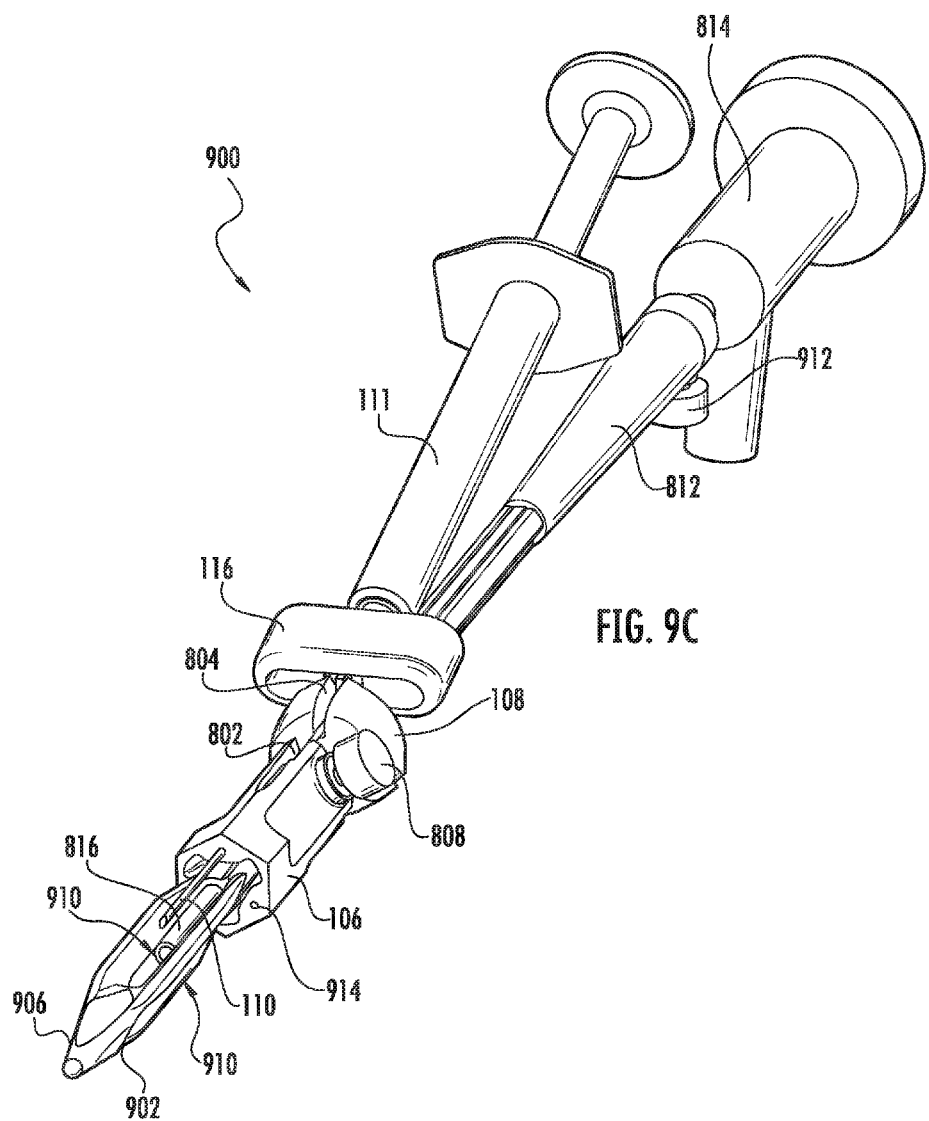

TARGETING THERAPEUTIC AGENTS

CROSS-REFERENCE TO RELATED APPLICATIONS

This application claims the benefit of U.S. Provisional Patent Application No. 61/230,905, filed Aug. 3, 2009, the disclosure of which is incorporated herein by reference in its entirety.

TECHNICAL FIELD

This disclosure relates to devices, systems, and methods for targeting therapeutic agents.

BACKGROUND

Therapeutic agents are commonly administered to subjects to treat numerous maladies. Often, it is desirable to target a therapeutic agent within a subject to achieve improved therapeutic results.

SUMMARY

Provided are devices, systems, and methods for targeted administration of therapeutic agents to a subject. For example, provided are devices, systems, and methods for targeting the administration of peri-urethral bulking agents.

The details of one or more aspects of the devices, systems and methods are set forth in the accompanying drawings and the description below. Other features, objects, and advantages will be apparent from the description and drawings, and from the claims.

DESCRIPTION OF DRAWINGS

FIG. 1 is a schematic diagram illustrating an example targeting device and system in a retracted position.

FIG. 2 is a schematic diagram illustrating an example targeting device and system in an extended position.

FIG. 3 is a schematic diagram illustrating an example targeting device and system in an extended position with a needle advanced for administering a therapeutic agent.

FIG. 4 is a schematic diagram illustrating a front-on view of the device and system of FIG. 1 in a retracted position.

FIG. 5 is a schematic diagram illustrating a front-on view of the device and system of FIGS. 2 and 3 in an extended position.

FIG. 8B is a schematic diagram illustrating an example targeting device and system in an extended position.

FIG. 9A is a schematic diagram illustrating an example targeting device and system.

FIG. 9C is a schematic perspective diagram illustrating an example targeting device and system.

DETAILED DESCRIPTION

Figure 6:
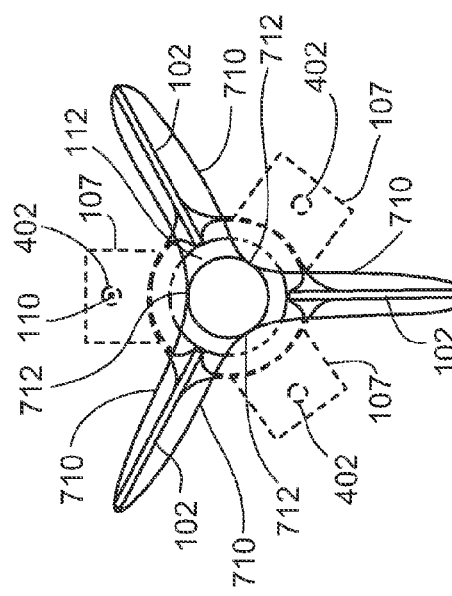
FIG. 6 is a schematic diagram illustrating a front-on view of the device and system of FIGS. 2 and 3 in an extended position and inserted into a subject.

The following detailed description should be read with reference to the drawings in which similar elements in different drawings are numbered the same. The drawings, which are not necessarily to scale, depict illustrative aspects and are not intended to limit the scope of what is claimed.

FIG. 1 is a schematic illustration of an example targeting device 100. Portions of the device 100 can be positioned within a lumen of a subject's organ. The device can be used to target administration of therapeutic agents. For example, the device can be used to target a therapeutic agent to a desired location near the extra-luminal surface of an organ to provide a therapeutic effect. Optionally, the device can be used to target a peri-urethral injection or injections of bulking agent. The targeted injection of peri-urethral bulking agent can treat urinary incontinence, including intrinsic sphincter deficiency (ISD) or type III stress urinary incontinence. Non-limiting examples of bulking agents include CONTIGEN® (C. R. Bard, Murray Hill, N.J.), DURASPHERE® (Carbon Medical Technologies, St. Paul, Minn.), COAPTITE® (Bioform Medical, San Mateo, Calif.), TEGRESS® (C. R. Bard, Murry Hill, N.J.), BULKAMID® (Contura, Soeborg, DK), MACROPLASTIQUE® (Uroplasty, Minneapolis, Minn.), and ZUIDEX® (Q-Med, Uppsala, Sweden). The therapeutic agent can also comprise energy from an energy source. For example, laser light energy or electrical energy are therapeutic agents that can be targeted using the described device, systems and methods.

The device 100 can comprise a rigid or semi-rigid sleeve 104 having a distal portion and a proximal portion. The rigid or semi-rigid nature of the sleeve allows the device or portions thereof to be inserted and advanced into an organ lumen of a subject. A lumen can extend the length of the sleeve and the sleeve can be open at its distal and proximal ends. The sleeve lumen can be sized to accept an optical lens device 112, which can be positioned and slidably moved within the sleeve lumen. The lens can also be selectively fixed in a desired location within the sleeve lumen. For example, the lens 112 can be inserted though the opening at the proximal end of the sleeve. The lens 112 can be advanced toward and through the distal end opening of the sleeve. Optionally, the lens is a 0° short cystoscope lens. The lens can have an outer coating and an inner optical portion as is common in cystoscope or other medical lenses. The lens can be coupled with an imaging device to allow further visualization within the lumen of the organ. For example, the lens can be coupled with a camera, a video device, an ultrasound imaging device, or another imaging device.

The device 100 further comprises an expandable frame. The frame can be expanded from a first retracted configuration to a second extended configuration. The first retracted position is adapted for insertion into the organ lumen and the second extended position is adapted to shape a concavity into an outer wall of an organ. An example of a concavity 712 is shown schematically in FIG. 6.

The frame can comprise a plurality of rigid or semi-rigid arms 102 each having a tip portion and a base portion. An arm is rigid or semi-rigid if, when it is expanded from the retracted to extended configuration, it can alter the shape of the organ in which it is located. For example, a rigid or semi-rigid arm can shape a concavity into the outer wall of an organ. The base portion of each arm 102 can be pivotably fixed about the distal opening of the sleeve 104. Each arm 102 is pivotable between a first retracted configuration in which each arm's tip is proximate to the central longitudinal axis (A) of the sleeve 104 as shown in FIG. 1, and an extended configuration in which the arms' tip portions are located more distant from the central longitudinal axis of the sleeve as shown in FIG. 2. The arms can be spaced about the sleeve such that, in their retracted position, the tips roughly approximate one another by converging about the longitudinal axis (A) at a point distal to the end of the sleeve. The pivotal fixation to the distal end of the sleeve can include, but is not limited to, a hinge with a hinge pin. The pivotal fixation can also include other connections between the arm and the sleeve that allow the arms to move between a retracted and an extended configuration. For example, the point of connection between the arms and the sleeve may be flexible such that it may flex between the refracted and extended configurations.

The arms 102 can be urged from their retracted configuration to their extended configuration by slidably advancing the lens 112 through the sleeve lumen and out the distal sleeve opening. In this regard, as the lens 112 is advanced through the distal sleeve opening, it can contact the arms to urge their tips away from the longitudinal axis (A) and into the extended position. Other mechanisms can also be used to extend the arms. For example an electronic actuator, a micromotor, a gear based mechanism, or another non-lens device configured for movement through the sleeve lumen, can be used to extend the arms.

Optionally, the device comprises three arms each having a base spaced about the distal sleeve such that in the retraced position the three tips approximate with each other as shown in FIG. 4. Optionally, the lens is selectively fixed in position after it has been advanced and the arms are in their extended configuration. For example, the lens 112 can comprise a notch located on its outer surface which can be mated to a tab located on the inner luminal wall of the sleeve 104. The tab can spring into the notch when the tab and notch are approximated to fix the lens 112 in a desired position within the sleeve 104. For example, the lens and sleeve can be rotated relative to each other to approximate the tab and the notch.

The device 100 can further comprise a guide apparatus. The guide apparatus can comprise a guiding portion 108 that is integral with or fixed to the sleeve 104. The guide apparatus can further comprise a slidable guiding member 106 that is slidable in a proximal or distal direction over the sleeve 104. The cross-sectional shape of the sleeve 104 can be triangular. Similarly, to allow for slidable movement over the triangular cross-sectional shape of the sleeve, the slidable guiding member 106 can have a corresponding triangular lumen. The guiding portion 108 is located proximal to the guiding member 106. The slidable guiding member 106 can also be selectively fixed in a position along the sleeve. For example, a similar fixing mechanism can be used as described above for fixing the lens within the sleeve lumen. In this regard, the guiding member 106 and the sleeve 104 can be mated to secure the guiding member 106 in a desired location on the sleeve. Both the guiding member 106 and the guiding portion 108 can include one or more guide projections (107 and 109). Optionally, in the case where the device has three arms, the guiding member and guiding portion each have three guide projections.

Each guide projection has a guide hole that allows passage of needle 110 or other administration device through the projection. The guide projections can be aligned with each other such that a needle can be directed through a guide hole of a projection 109 and into and through a guide hole of a projection 107. Moreover, the aligned guide projections can be further aligned with the space between the extended arms 102, as best shown in FIG. 3 and FIG. 4. The height of each protrusion (107 and 109) and of the corresponding guiding hole is such that when the needle 110 is inserted into the subject's tissue, the needle path in on the outside of the organ wall to allow for administration of a therapeutic agent about the outside organ wall. The needle can be the needle of a commercially available peri-uretheral bulking agent kit.

Figure 8A:
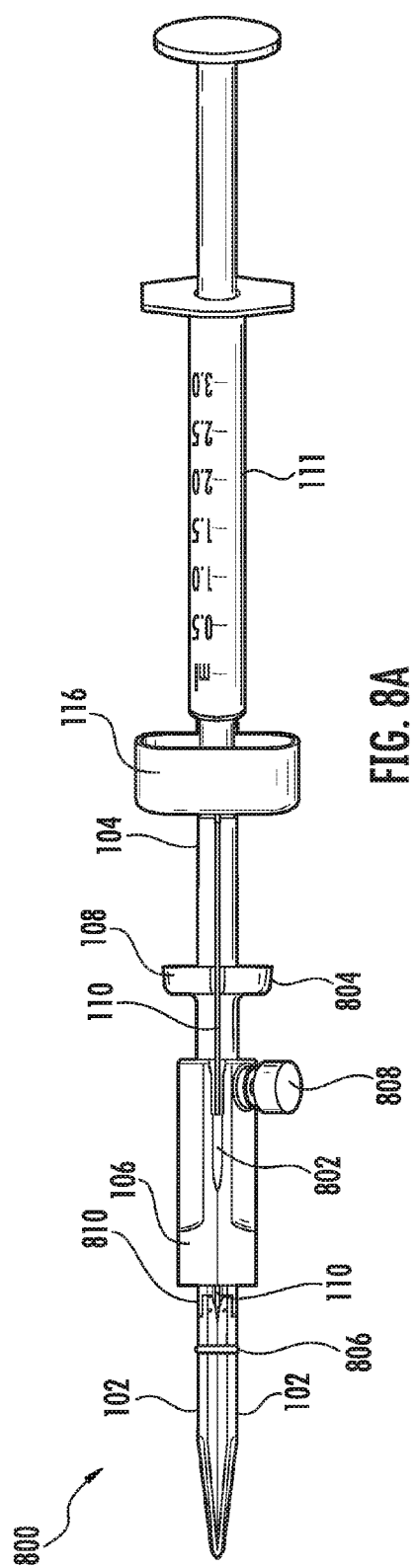
FIG. 8A is a schematic diagram illustrating an example targeting device and system in a retracted position.

Referring now to FIGS. 8A and 8B, an example device 800 is shown. The device 800 comprises and expandable frame as described above. The device 800 can further comprises a mechanism for biasing the arms towards the non-expanded position, such as elastic o-ring 806. The o-ring can function to keep the arms generally in a non-expanded position during insertion of the frame into an organ lumen such as into the urethra. The o-ring can also allow extension of the arms as described herein and as shown in FIG. 8B. Other mechanism of biasing can also be used in addition or instead of an o-ring. For example, springs can be used to bias the arms towards their retracted position.

The device 800 includes a guidance slot 804 defined in the guiding portion 108. The guiding member 106 can also include a guiding slot 802. The guiding slot 802 is in communication with a lumen that extends to the distal end of the guiding member 106 and which opens on the distal extend of the guiding member. The guiding slot and the lumen allow and guide passage of an administration device such as needle into the subject. The direction of the slots, lumen and opening can be aligned such that an administration device, such as a needle 110, can be guided into proximity with the shaped concavity for administration of a therapeutic agent, such as a periurethral bulking agent. In some aspects, there can be multiple lumens and openings at varying distances as measured perpendicular to the long central axis of the frame to allow administration of therapeutic agent at multiple distances from the central long axis of the frame. The use of a slot in the guiding member 106 and/or guiding portion can enhance efficiency of positioning of the administration device into the subject.

The device 800 can also be used with a scope 814 and 816 for visualization of the intraluminal aspects of the urethra. For example, the scope can be used to visualize one or more shaped concavities in the urethra. The distal end of the scope can be limited in its depth of penetration into the urethra with a stopping mechanism 812. The stopping mechanism 812 is described below in greater detail with reference to FIGS. 9A-C.

Figure 9B:
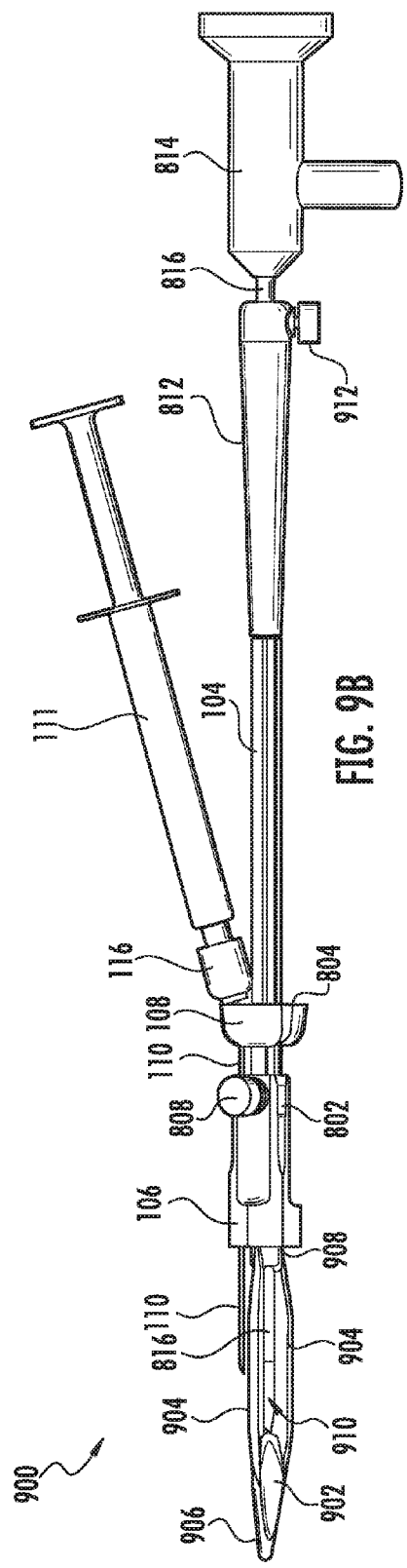
FIG. 9B is a schematic diagram illustrating an example targeting device and system.

FIGS. 9A-C are schematic illustrations of an example targeting device 900. Portions of the device 900 can be positioned within a lumen of a subject's organ. As with the device 100 and 800, the device 900 can be used to target administration of therapeutic agents. For example, the device 900 can be used to target a therapeutic agent to a desired location near the extra-luminal surface of an organ to provide a therapeutic effect. Optionally, the device can be used to target a peri-urethral injection or injections of bulking agent. The targeted injection of peri-urethral bulking agent can treat urinary incontinence, including intrinsic sphincter deficiency (ISD) or type III stress urinary incontinence.

Non-limiting examples of bulking agents include CONTIGEN® (C. R. Bard, Murray Hill, N.J.), DURASPHERE® (Carbon Medical Technologies, St. Paul, Minn.), COAPTITE® (Bioform Medical, San Mateo, Calif.), TEGRESS® (C. R. Bard, Murry Hill, N.J.), BULKAMID® (Contura, Soeborg, DK), MACROPLASTIQUE® (Uroplasty, Minneapolis, Minn.), and ZUIDEX® (Q-Med, Uppsala, Sweden). The therapeutic agent can also comprise energy from an energy source. For example, laser light energy or electrical energy are therapeutic agents that can be targeted using the described device, systems and methods.

The device 900 can comprise a rigid or semi-rigid frame having at least one rib member 904. For example, as shown in FIGS. 9A-C the device 900 can have three or more rib members. Each rib member can extend from a distal portion 908 of a sleeve 104. As described above, the sleeve 104 can have a proximal and distal opening and a lumen extending between the openings The rib members 904 can extend distally from the distal portion of the sleeve 104 and can terminate at a proximal portion of the frame 902. The distal frame portion 902 can have a tip 906. The tip 906 can aid insertion and advancement of the frame into and through the lumen of a subject's urethra.

One or more voids 910 are defined between one or more, or optionally, all rib members. The rib members 904 can act to shape a concavity in the outer wall of the urethra by supplying two locations of tension inside the urethra lumen. The portion of the luminal wall of the urethra between the two rib members can droop or sag into a void 910. The outer wall of the urethra corresponding to the droop or sag can be targeted for the peri-urethral bulking agent.

The device 900 can further comprise a guide apparatus including a guiding member 106 and a guiding portion that can be used in guiding the peri-urethral bulking agent into the shaped concavity. In this regard, the guiding member 106 can be slidably positioned on the sleeve 104. The guiding member can slide proximally and distally along the length of the sleeve 104. At any desired position of the guiding member 106 relative to the length of the sleeve, the guiding member can be secured in position. For example, a set screw 808 can be used to permanently or temporarily secure the guiding member in a desired position along the length of the sleeve 104.

The guide apparatus can further comprise a guiding portion 108 positioned proximal to the guiding member 106. The guiding portion 108 may be fixed to the sleeve 104 as described above in relation to the device 100. Also as described above, distal movement of the guiding member 106 allows deeper insertion of the frame into the urethra and proximal movement of the guiding member 106 allows shallower insertion of the frame into the urethra. Thus, by adjusting the location of the guiding member 106 along the length of the sleeve 104, the depth of the frame in the urethra can be adjusted.

Because the depth of the frame in the urethra can be adjusted, the location of the concavity along the length of the urethra can be adjusted. Also, since the frame can be rotated or inserted into the urethra in different rotational positions, the concavity can be both positioned at different lengths of the urethra and at different rotational positions.

The device 900 includes a guidance slot 804 defined in the guiding portion 108. The guiding member 106 can also include a guiding slot 802. The guiding slot 802 is in communication with a lumen that extends to the distal end of the guiding member 106 and which opens on the distal extend of the guiding member at an opening 914. The guiding slots and the lumen allow and guide passage of an administration device such as needle into the subject. The direction of the slots, lumen and opening 914 can be aligned such that an administration device, such as a needle 110, can be guided into proximity with a shaped concavity positioned above a void 910 for administration of a therapeutic agent, such as a periurethral bulking agent. In some aspects, there can be multiple lumens and openings at varying distances as measured perpendicular to the long central axis of the frame. This allows administration of therapeutic agent at multiple distances from the central long axis of the frame. The use of a slot in the guiding member 106 and/or guiding portion can enhance efficiency of positioning of the administration device into the subject.

As described above in relation to the example device 800, the device 900 can be used with a scope 814 and 816. The distal end of the scope can be advanced into the urethra for visualizing the lumen and the intraluminal walls of the urethra. For example, one or more shaped concavity can be visualized using the scope. The depth of penetration of the scope into the lumen of an organ can be controlled by a stopping mechanism 812.

The stopping mechanism comprises a distal end having an opening, a proximal end having an opening, and passage connecting the distal and proximal openings. The openings and passage have a sufficient diameter to allow for the slidable passage of portions of the scope. The stopping mechanism also is dimensioned, however, to contact and stop against a portion of the sleeve 104. For example, the distal end of the stopping mechanism can abut with the proximal end of the sleeve 104 as shown in FIGS. 9B and 9C. The stopping mechanism 812 further includes a mechanism for being secured to the scope. For example, the stopping mechanism may comprise a set screw 912 which can engage and secure the stopping mechanism to the scope. In this way, the relative movement of the scope and the stopping mechanism is prevented. In addition, because the stopping mechanism is prevented from relative movement in relation to the sleeve by abutting with the sleeve, the scope is prevented from further distal insertion into the organ. Thus, the stopping mechanism 812 can be used to select a desired depth of penetration of the scope into an organ lumen.

The administration device for use with the example targeting devices described, such as a needle 110 can include any device for depositing therapeutic agent into a subject. One example device is a syringe device. The needle can be a component of a syringe device. Although a needle is used by way of example throughout, a cannula or any other portion of an administration device configured for depositing or applying a therapeutic agent in a subject can be guided to for targeted administration using the devices, systems and methods. The syringe device can further comprise a hub portion 116, a barrel portion 111, and a plunger portion. The barrel portion 111, can be loaded with a therapeutic agent for administration to the subject. For example, the barrel 111 can be loaded with a bulking agent for peri-urethral administration to treat urinary incontinence.

As is typical with a syringe, depression of the plunger can force the therapeutic agent through the needle and into the subject's tissue. Thus, with an expandable frame device, when the arms 102 are extended, the needle can be advanced through the guide projections and into the subject's tissue. The needle can be advanced distally until the hub rests against the guide projection 109 as shown in FIG. 3. The needle can also be advanced until the hub rests against a portion of the guiding portion 108 as shown in FIGS. 8B, 9B and 9C. Because the guiding portion 108 is integral or fixed to the sleeve, distal advancement of the needle is limited by the syringe hub abutting with the guide projection 109 or guiding portion 108, since the guide hole is not large enough to allow for passage of the hub.

When fully advanced, the needle tip is positioned a predetermined distance from the guiding portion 108. Because the arms 102 or ribs 904 are also fixed relative to the sleeve 104 and the guiding portion 108, the needle tip when fully advanced is also positioned at a predetermined distance along the arms' or ribs' length. Because the slidable guiding member 106 is moveable relative to the guiding portion 108 and the arms 102 or ribs 904, however, the distance the needle 110 projects into the subject's tissue and the distance the arms or ribs project into the organ lumen are variable. Thus, the desired depth of administration of therapeutic agent to the subject can be varied by altering the position of the slidable guiding member 106 along the length of the sleeve 104.

The described devices can be used to target the administration of a urethral bulking agent to a subject having urinary incontinence. For example, in operation, portions of the devices can be directed into the lumen of an organ. The devices can be used to administer therapeutic agents in an extraluminal location. For example, portions of the devices can be directed into the urethral lumen of a subject and urethral bulking agents can be administered extraluminally to treat urinary incontinence. The extraluminal administration can comprise a peri-urethral injection of bulking agent. Treatment can include reducing symptoms of urinary incontinence, including a partial or a complete reduction of any symptoms of incontinence experienced by a subject. Thus, a therapeutic agent is one that is used to reduce one or more symptoms of a malady, such as urinary incontinence.

The devices can also be used for treatment in other organs having lumens. For example, portions of the devices can be interested into an esophagus, trachea, anus, or rectum and agents can be administered in a location extraluminal to these organs. Thus, peri-esophageal, peri-tracheal, peri-anal and peri-rectal targeted administrations can be made. By example only, and in regard to the urethra, the arms 102 or ribs 904 can be directed into the urinary meatus and advanced forward into the urethral lumen. The arms or ribs can be advanced a desired distance including to an extent where the arm tips or rib tips reach the bladder neck.

Figure 7:
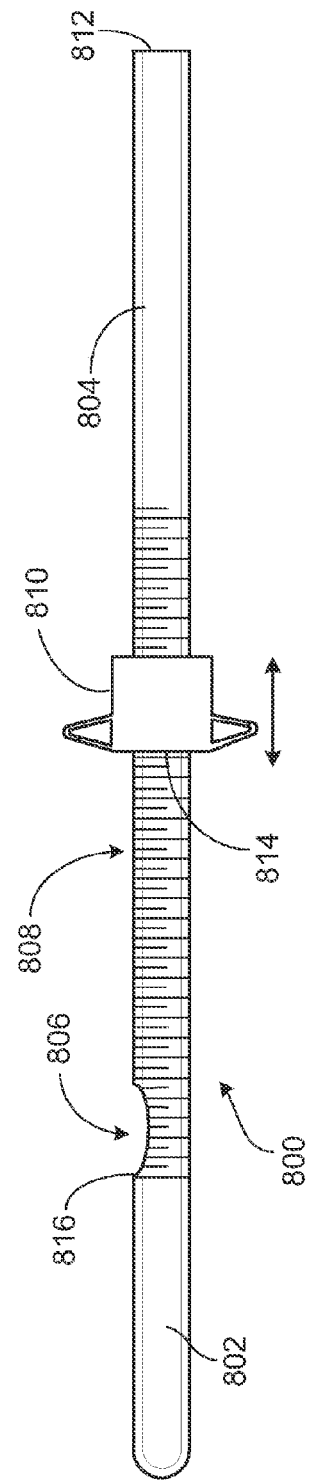
FIG. 7 is a schematic diagram illustrating a urethral measurement device.

To target the administration, the urethral length is measured. For example, the measuring device 800 shown schematically in FIG. 7 can be used to measure the urethral length. The measuring device 800 comprises a conduit 802 having a distal end and a proximal end. The device further comprises an opening 806, which is in fluid communication with a lumen of the conduit and the proximal end 812 of the device, which is open.

The distal end is inserted into a subject's urethra and advanced toward the bladder. The distal end eventually enters the bladder and the device is advanced until the opening 806 enters the bladder. Once the opening 806 enters the bladder, urine flows into the opening 806, through the lumen of the conduit, and out the open proximal end 812 of the device. Urine flowing out of the open proximal end 812 of the device indicates that the opening 806 has entered the bladder. When the opening 806 is positioned just inside the proximal urethra, the flow stops and the slidable block 810 is moved distally about the conduit 802 until its distal surface 814 rests against the external urinary meatus of the subject. The distance between the distal surface 814 of the slidable block 810 and the distal edge 816 of the opening 806 approximates the subject's urethral length. Optionally, the slidable block 810 has the same shape as the guiding member 106. Optionally, the slidable block is the guiding member 106.

Measurement of urethral length can also be accomplished using a traditional Foley catheter design. A slidable block can be positioned on the catheter shaft and moved along a graduated scale located on the catheter shaft. The catheter can be inserted through the urethra and into the bladder. The balloon of the catheter can be inflated in the bladder and the catheter can be drawn back so that the balloon rests on the bladder base. The slidable block can then be advanced to the external urinary meatus. The distance between the inflated balloon and the slidable block can approximate the urethral length.

The approximated urethral length can be used to determine the position where the guiding member 106 should be fixed along the sleeve 104 based on the desired location for administration of the urethral bulking agent along the urethra. Because the needle extends to a fixed distance relative to the arms 102 or ribs 904 and sleeve 104 when fully advanced, the position of the needle 110 tip within the subject can be varied by varying the position of the guiding member 106 along the sleeve 104. Thus, if the guiding member 106 is fixed more proximally along the sleeve 104 toward the guiding portion 108, the arms 102 or ribs 904 and needle 110 extend further into the subject. If the guiding member 106 is fixed more distally along the sleeve 104 away from the guiding portion 108, the arms 102 or ribs 904 and needle 110 extend less deeply into the subject.

Given the measured length of the urethra and the desired position to administer therapeutic agent along the urethral length, the position to fix the guiding member 106 along the sleeve length can be readily determined. Once the proper position for the guiding member 106 is determined, it can be fixed to the sleeve 104 along graduated markings located on the sleeve.

In example devices with an expandable frame, the lens 112 can be loaded into the sleeve lumen for actuating the expansion of arms to the extended position once the device is properly positioned.

The device frames can be inserted into the external urinary meatus and the device can be advanced into the urethra until the distal surface 105 of the guiding member 106 comes to abut the external urinary meatus. In example devices with an expandable frame, the lens 112 can be advanced distally through the sleeve lumen to urge the arms into their extended position within the urethral lumen. The extension of the arms alters the shape of the urethral lumen. When three arms are used, the arms tend to triangulate the urethra of the subject. Once the lens 112 has been advanced to extend the arms, it can be fixed in position, which also acts to fix the arms 102 in their extended position. The lens 112 can be coupled to an imaging device for visualizing the interior of the urethra.

When the arms 102 are extended, the urethral tissue 710 between the arms will sag to form a depression or concavity 712 in the outer organ wall with a corresponding inward convexity between each extended arm as shown in FIG. 6. The inward convexity can be visualized using the lens and coupled imaging device from inside the organ lumen. The outer organ wall depressions or concavities correspond to the desired location for administering the therapeutic bulking agent. Similar anatomic changes to the urethral tissue are achieved using a frame that is not expandable such as the example devices shown in FIGS. 9A-9C.

The needle 110 tip, when fully advanced until its hub 116 abuts the proximal surface 113 of the protrusion 109 or guiding portion 108 is positioned external to the urethral lumen in a location where administered agent accumulates in the depression or concavity. The administration can be made in the organ wall of the concavity or external to the organ wall in the concavity. Optionally, the needle is positioned at the midway point between the arms at the low point of the concavity. Optionally, the needle is beveled and the bevel tip is directed towards the concavity. The needle can also be a non-beveled type. Once the needle is advanced into this position, agent can be administered by advancing the syringe plunger.

The distance between the administration site and the shaped concavity can also vary in a direction perpendicular to the central longitudinal axis (A) of the sleeve 104. For example, this distance can be modified by raising or lowering the administration device, such as a needle 110, away or towards the other surface of the sleeve 104. When the needle is raised further from the outer surface of the sleeve it can target therapeutic agent higher above the shaped concavity compared to lower positions of the needle to the outer surface of the sleeve. In some examples, the distance between the outer surface of the sleeve 104 and the needle 110 measured along a plane generally perpendicular to the central longitudinal axis (A) of the sleeve 104 can be between about 1.0 millimeters (mm) and 7.0 millimeters (mm). For example, the distance can be between about 2.0 mm and about 4.5 mm, or between about 3.0 mm and 2.5 mm. These measurements can also correspond to the distance between the bottom of the concavity 712 and administration site. For example, the measurements can correspond to the distance between the the guide hole 402 or needle 110 and the bottom of the concavity 712 as shown in FIG. 6.

The concavity or depression can be identified or located by visualizing a corresponding inward convexity from inside the urethra by using the lens 112 and imaging device and/or a scope 814 and 816. After administering a desired amount of agent into the depression or concavity between two of the arms, the needle can be removed and inserted through a second set of aligned guiding portion projections 109 and guiding member projections 107, or through a second set of aligned guide slots 804 and 802, which target the needle 110 to the same depth as the first administration, but in a different depression or concavity formed by at least one further arm 102 or at least one further rib 904.

For a device comprising three arms or three ribs, this process can be repeated once more to administer agent into a third depression or concavity created by the three extended arms or three ribs. If four arms or ribs are used, then four depressions can be created, each of which can have agent administered thereto. Administration can be made to less than the total number of created depressions or concavities. Optionally, three administrations of bulking agent can be made at about the 5 o'clock, 8 o'clock and 1 o'clock positions.

The devices can be removed by retracting the needle 110 from the subject. The lens 112 can also be unfixed from the sleeve 104 and the lens can be backed proximately out of the sleeve lumen. If an expandable frame device is used, as it is backed out of the lumen, the arms can return to their retracted position and the device can be removed from the subject.

A system is also provided for targeting administration of a therapeutic agent to a subject. The system can comprise a device having an expandable frame sized for insertion into an organ lumen. The frame can shape a concavity in an organ. Optionally, the frame has a first retracted configuration and a second extended configuration. The second extended configuration can be adapted to shape a concavity into an outer wall of the organ. The device of the system can further comprise a guide apparatus adapted to guide an administration device external to the organ lumen and proximate to the shaped concavity such that therapeutic agent administered from the administration device locates in the shaped concavity. The system can further comprise an actuator for urging the expandable frame from its first retracted configuration to its second extended configuration. Optionally, the actuator comprises an optical device, such as a lens. The system can further comprise an administration device, such as a syringe, comprising a peri-urethral bulking agent.

The described devices can be made of molded plastic or any other suitable material such as stainless steel. Common materials that can be used are routinely used in medial and surgical devices. The devices can be packaged sterilely, and can be disposable after each use. A number of aspects of the systems, devices and methods have been described.

Nevertheless, it will be understood that various modifications may be made without departing from the spirit and scope of the disclosure. Accordingly, other aspects are within the scope of the following claims.

What is claimed is:

1. A device for targeting administration of a therapeutic agent to a subject, comprising:
   a sleeve having a proximal end and a distal end and defining a lumen that is open at the proximal end and the distal end;
   a frame for insertion into an organ lumen, wherein the frame is adapted to shape a concavity into an outer wall of the organ and a portion of the frame is disposed about the distal end of the sleeve; and
   a guide apparatus positioned on the sleeve and adapted to guide an administration device external to the sleeve and the organ lumen and proximate to the shaped concavity, wherein the guide apparatus includes a guiding member that is slidable along the sleeve.

2. The device of claim 1, wherein the frame comprises a proximal portion and a distal portion and at least two rib members extend between the proximal and distal portions.

3. The device of claim 2, wherein each rib member has a length between the proximal and distal portions of the frame and wherein at least two of the rib members are spaced from each other along at least a portion of the length between the proximal and distal portions.

4. The device of claim 3, wherein a void is defined between the portion of the rib members that are spaced apart from each other.

5. The device of claim 4, wherein the concavity shaped into an outer wall of the organ is formed between the portion of the rib members that are spaced apart from each other.

6. The device of claim 5, wherein the concavity is shaped in the void.

7. The device of claim 2, wherein the proximal portion has a cone shape.

8. The device of claim 1, wherein an optical device is positionable and slidable within the sleeve lumen.

9. The device of claim 1, further comprising at least two rib members that extend distally from the distal end of the sleeve in a direction a long axis of the sleeve.

10. The device of claim 9, wherein at least two of the rib members are spaced from each other along at least a portion of their length between the proximal and distal portions.

11. The device of claim 10, wherein a void is defined between the portion of the rib members that are spaced apart from each other.

12. The device of claim 11, wherein the concavity shaped into an outer wall of the organ is formed between the portion of the rib members that are spaced apart from each other.

13. The device of claim 12, wherein the concavity is shaped in the void.

14. The device of claim 9, further comprising a distal point portion,
   wherein at least two of the rib members terminate at the distal point portion proximal to a tip of the distal point portion.

15. The device of claim 1, wherein the frame is sized to fit into the urethra of the subject.

16. The device of claim 15, wherein the concavity is shaped in the outer wall of the urethra.

17. The device of claim 16, wherein the therapeutic agent is administered proximate to the shaped concavity in the urethra.

18. The device of claim 17, wherein the therapeutic agent is a peri-uretheral bulking agent.

19. The device of claim 1, wherein the frame has a first retracted configuration and a second extended configuration, the first retracted configuration adapted to be inserted into the organ lumen and the second extended configuration adapted to shape a concavity into an outer wall of the organ.

20. The device of claim 19, further comprising an actuator for urging the frame from the first retracted configuration to the second extended configuration.

21. The device of claim 19, wherein the frame is adapted to shape a plurality of concavities into an outer wall of the organ.

22. The device of claim 19, wherein the frame comprises a plurality of arms each having a distal tip portion and a proximal base portion.

23. The device of claim 22, wherein an elastic ring is positioned around a periphery of the arms such that the ring provides a biasing force that urges the arms together towards the retracted configuration of the frame.

24. The device of claim 22, wherein the base portion of each arm is pivotably fixed about the distal end of the sleeve.

25. The device of claim 24, wherein:
the sleeve has a central longitudinal axis, and
the base portion of each arm is pivotably fixed about the distal end of the sleeve.

26. The device of claim 25, wherein:
the frame has a first retracted configuration and a second extended configuration;
the first retracted configuration includes the tip portion of each of the plurality of arms converging about the central longitudinal axis; and
the second extended configuration includes the tip portion of each of the plurality of arms extending away from the central longitudinal axis.

27. The device of claim 1, wherein an optical device is positionable and slidable within the sleeve lumen.

28. The device of claim 27, wherein sliding the optical device is configured to actuate expansion of the frame from the first refracted configuration to its the second extended configuration when the optical device is slid through the distal end of the sleeve.

29. The device of claim 28, wherein the optical device is a lens.

30. The device of claim 29, wherein the lens is adapted for coupling to an imaging device to allow visualization inside the organ lumen.

31. The device of claim 1, wherein the guide apparatus comprises a guiding portion integral with or fixed to an outer wall of the sleeve, the guiding portion having a hole spaced from the outer wall of the sleeve and adapted for the passage there through of the administration device.

32. The device of claim 31, wherein the guiding member is slidable along the outer wall of the sleeve and positioned about the sleeve distal to the guiding portion.

33. The device of claim 32, wherein the guiding member comprises a hole spaced from the outer wall of the sleeve and adapted for the passage there through of the administration device.

34. The device of claim 33, wherein the administration device is a needle of a syringe.

35. The device of claim 33, wherein the guiding member is adapted to be fixed in a desired location about the sleeve.

36. The device of claim 1, further comprising a measuring device for measuring urethral length.

37. The device of claim 1, wherein:
the guiding member includes one or more guide projections adapted for passage there through of the administration device.

38. The device of claim 1, wherein the frame includes a proximal portion and a distal portion, the proximal portion of the frame is fixed about the distal end of the sleeve.

39. A system for targeting administration of a therapeutic agent to a subject, comprising:
a sleeve having a proximal end and a distal end and defining a lumen that is open at the proximal end and the distal end, the sleeve having a central longitudinal axis;
an expandable frame sized for insertion into an organ lumen, the frame including a plurality of arms, each arm having a distal tip portion and a proximal base portion, the base portion of each arm being pivotably fixed about the distal end of the sleeve, the frame having a first retracted configuration and a second extended configuration, the first retracted configuration adapted to be inserted into the organ lumen and the second extended configuration adapted to shape a concavity into an outer wall of the organ, the first retracted configuration including the tip portion of each of the plurality of arms converging about the central longitudinal axis and the second extended configuration including the tip portion of each of the plurality of arms extending away from the central longitudinal axis;
a guide apparatus positioned on the sleeve and adapted to guide an administration device external to the organ lumen and proximate to the shaped concavity; and
an actuator configured to urge the expandable frame from the first retracted configuration to the second extended configuration.

40. The system of claim 39, wherein the expandable frame is adapted to shape a plurality of concavities into an outer wall of the organ.

41. The system of claim 39, wherein the actuator is an optical device that is positionable and slidable within the sleeve lumen.

42. The system of claim 41, wherein the optical device is configured to actuate expansion of the frame from the first refracted configuration to the second extended configuration when the optical device is slid through the distal end of the sleeve.

43. The system of claim 42, wherein the optical device is a lens.

44. The system of claim 43, wherein the lens is adapted for coupling to a imaging device to allow visualization inside the organ lumen.

45. The system of claim 39, wherein the guide apparatus comprises a guiding portion integral with or fixed to an outer wall of the sleeve, the guiding portion having a hole spaced from the outer wall of the sleeve and adapted for the passage there through of the administration device.

46. The system of claim 45, wherein the guide apparatus further comprises a guiding member slidable along the outer wall of the sleeve and positioned about the sleeve distal to the guiding portion.

47. The system of claim 46, wherein the guiding member comprises a hole spaced from the outer wall of the sleeve and adapted for the passage there through of the administration device.

48. The system of claim 47, wherein the administration device comprises a needle of a syringe.

49. The system of claim 48, wherein the administration device further comprises a syringe barrel configured to be filled with the therapeutic agent to be administered to the subject.

50. The system of claim 49, wherein the therapeutic agent is a peri-urethral bulking agent.

51. The system of claim 47, wherein the guiding member is adapted to be fixed in a desired location about the sleeve.

52. The system of claim 39, further comprising a measuring device for measuring urethral length.

53. The system of claim 39, wherein the guide apparatus further comprises a guiding member and a guiding portion disposed about the sleeve, the guiding portion being located proximal to the guiding member with respect to the distal end of the sleeve.

54. The system of claim 53, wherein each of the guiding member and the guiding portion includes one or more guide projections adapted for passage there through of the administration device.

55. A system for targeting administration of a therapeutic agent to a subject, comprising:
- a sleeve having a proximal end and a distal end and defining a lumen that is open at the proximal end and the distal end;
- a frame for insertion into an organ lumen, the frame being adapted to shape a concavity into an outer wall of the organ, the frame including a plurality of arms, each arm having a distal tip portion and a proximal base portion, the base portion of each arm being spaced about and pivotably fixed about the distal end of the sleeve, and extending from the distal end of the sleeve to a point distal to the distal end of the sleeve; and
- a guide apparatus positioned on the sleeve and adapted to guide an administration device external to the organ lumen and proximate to the shaped concavity.

56. The system of claim 55, wherein:
the sleeve has a central longitudinal axis;
the frame has a first retracted configuration and a second extended configuration;
the first retracted configuration includes the tip portion of each of the plurality of arms converging about the central longitudinal axis; and
the second extended configuration includes the tip portion of each of the plurality of arms extending away from the central longitudinal axis.

57. The system of claim 55, wherein:
the guide apparatus further comprises a guiding member and a guiding portion disposed about the sleeve, the guiding portion being located proximal to the guiding member with respect to the distal end of the sleeve.

58. The system of claim 57, wherein each of the guiding member and the guiding portion includes one or more guide projections adapted for passage there through of the administration device.

* * * * *